(12) United States Patent
Jackson et al.

(10) Patent No.: US 7,163,930 B2
(45) Date of Patent: *Jan. 16, 2007

(54) PHARMACEUTICAL COMPOSITIONS AND METHODS RELATING TO FUCANS

(75) Inventors: John K. Jackson, Vancouver (CA); Helen M. Burt, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/958,759

(22) Filed: Oct. 5, 2004

(65) Prior Publication Data

US 2005/0119216 A1 Jun. 2, 2005

(51) Int. Cl.
*A61K 31/737* (2006.01)

(52) U.S. Cl. .................. 514/54; 514/11; 514/27; 514/34; 514/44; 514/171; 514/251; 514/283; 514/449; 514/559; 514/681; 514/682

(58) Field of Classification Search .............. 514/44, 514/11, 34, 54, 171, 251, 283, 449, 559, 681, 514/682, 27
See application file for complete search history.

(56) References Cited

U.S. PATENT DOCUMENTS

| 5,705,177 | A | * | 1/1998 | Roufa et al. | ........... 424/422 |
| 6,020,326 | A | * | 2/2000 | Roufa et al. | ............... 514/59 |
| 6,559,131 | B1 | | 5/2003 | Senni et al. | |

FOREIGN PATENT DOCUMENTS

| EP | 0 293 826 | | 12/1988 |
| EP | 0 645 143 | | 3/1995 |
| EP | 0645143 | B1 | 5/2000 |
| FR | 2 772 618 | | 6/1999 |
| FR | 2772618 | | 6/1999 |
| JP | 01-031707 | | 2/1989 |
| JP | 64-085905 | | 3/1989 |
| JP | 01-313433 | | 12/1989 |
| WO | WO 92/19761 | * | 11/1992 |
| WO | WO 01/82936 | | 11/2001 |

OTHER PUBLICATIONS

PCT International Search Report, PCT/CA02/01337, Dec. 20, 2002.
Bittuon, Patrick, et al., Low-Molecular-Weight Dextran Derivatives (*f*-CMDB) Enter The Nucleus And Are Better Cell-Growth Inhibitors Compared With Parent CMDB Polymers, Carbohydrate Research, vol. 322, pp. 247-255 (1999).
Blondin, Catherine, et al., Inhibition of Complement Activation by Natural Sulfated Polysaccharides (Fucans) From Brown Seaweed, Molecular Immunology, vol. 31, No. 4, pp. 247-253 (1994).
Brandley, Brian K., et al., Multiple Carbohydrate Receptors on Lymphocytes Revealed by Adhesion to Immobilized Polysaccharides, J. Cell Biology, vol. 105, pp. 991-997 (1987).

Giraux, Jean-Luc, et al., Modulation of Human Endothelial Cell Proliferation and Migration by Fucoidan and Heparin, European J. Cell Biology, vol. 77, pp. 352-359 (1998).
Glabe, Charles G., et al., Reversible Disruption of Cultured Endothelial Monolayers by Sulphated Fucans, J. Cell. Sci., vol. 61, pp. 475-490 (1983).
Itoh, Hiroko, et al., Antitumor Activity and Immunological Properties of Marine Algal Polysaccharides, Especially Fucoidan, Prepared from *Sargassum thunbergii* of Phaeophyceae, Anticancer Research, vol. 13, pp. 2045-2052 (1993).
Itoh, Hiroko, et al., Immunological Analysis of Inhibition of Lung Metastases by Fucoidan (GIV-A) Prepared From Brown Seaweed *Sargassum thunbergii*, Anticancer Research, vol. 15, pp. 1937-1948 (1995).
Logearet, Delphine, et al., Fucans, Sulfated Polysaccharides Extracted From Brown Seaweeds, Inhibit Vascular Smooth Muscle Cells Proliferation. I. Comparison With Heparin For Antiproliferative Activity, Binding and Internalization, European J. Cell Biology, vol. 74, pp. 376-384 (1997).
Logearet, Delphine, et al., Fucans, Sulfated Polysaccharides Extracted From Brown Seaweeds, Inhibit Vascular Smooth Muscle Cells Proliferation. II. Degradation and Molecular Weight Effect, European J. of Cell Biology, vol. 74, pp. 385-390 (1997).
Mauray, S., et al., Comparative Ainticoagulant Activity and Influence on Thrombin Generation of Dextran Derivatives and a Fucoidan Fraction, J. Biomater. Sci. polymer. Edn., vol. 9, No. 4, pp. 373-387 (1998).
Nishino, T., et al., Antithrombin Activity of a Fucan Sulfate From The Brown Seaweed *Ecklonia kurome*, Thrombosis Research , vol. 62, pp. 765-773 (1991).
Patankar, Manish S., et al., A revised Structure for Fucoidan May Explain Some of Its Biological Activities, J. Biol. Chem., vol. 268, No. 29, pp. 21770-21776 (1993).
Pereira, Mariana S., et al., Structure and Anticoagulant Activity of Sulfated Fucans, J. Biol. Chem., vol. 274, No. 12, pp. 7656-7667 (1999).
Riou, D., et al., Antitumor and Antiproliferative Effects of a Fucan Extracted From *Ascophyllum nodosum* Against a Non-Small-Cell Bronchopulmonary Carcinoma Line, Anticancer Research, vol. 16, pp. 1213-1218 (1996).
Shibata, Hideyuki, et al., Inhibitory Effect of *Cladosiphon* Fucoidan on the Adhesion of *Helicobacter pylori* to Human Gastric Cells, J. Nutr. Sci. Vitaminol., vol. 45, pp. 325-336 (1999).
Soeda, Shinji, et al., Oversulfated Fucoidan Inhibits the Basic Fibroblast Growth Factor-Induced Tube Formation by Human Umbilical Vein Endothelial Cells: its Possible Mechanism of Action, Biochemica et Biophysica Acta, vol. 1497, pp. 124-134 (2000).
Examination Report for New Zealand Application No. 532015, Apr. 29, 2005.

* cited by examiner

*Primary Examiner*—Shaojia A. Jiang
*Assistant Examiner*—Ganapathy Krishnan
(74) *Attorney, Agent, or Firm*—Joshua King; Graybeal Jackson Haley LLP

(57) ABSTRACT

Compositions, methods and the like comprising fucans such as fucoidan to treat surgical adhesions, arthritis, and psoriasis.

15 Claims, 3 Drawing Sheets

PHARMACEUTICAL COMPOSITIONS AND METHODS RELATING TO FUCANS

CROSS-REFERENCE TO RELATED APPLICATIONS

The present application claims priority from U.S. patent application Ser. No. 10/232,850, filed Aug. 28, 2002 now U.S. Pat. No. 6,812,220, currently pending, which application claims priority from U.S. provisional patent application No. 60/315,362, filed Aug. 29, 2001.

BACKGROUND

A surgical adhesion is a type of scar that forms between two parts of the body, usually after surgery. Adhesions can cause severe problems. For example, adhesions involving the female reproductive organs (ovaries, Fallopian tubes) can cause infertility, dyspareunia (painful intercourse) and severe pelvic pain. Adhesions that occur in the bowel can cause bowel obstruction or blockage, and adhesions can also form in other places such as around the heart, spine and in the hand. In addition to surgery, adhesions can be caused by things such as endometriosis, infection, chemotherapy, radiation and cancer.

Adhesions, as well as other angiogenic related diseases such as arthritis and psoriasis, can last for weeks, months or years, requiring extended and costly care. See *Robbins Pathological Basis of Disease* by Cotran, R. S., Kumar, V., Robbins, S. L., p75 (W. B. Saunders Co., 1989). Such diseases and conditions can develop into chronic inflammatory conditions with terrible consequences to both the mental and physical well-being of the patient. Unfortunately, there are few therapeutic options for patients with surgical adhesions, arthritis, and psoriasis. Often patients are treated with drugs such as steroidal or non-steroidal anti-inflammatories to relieve the symptoms of the diseases. However, these therapies may not offer adequate long-term benefit and are associated with serious side effects if used too frequently (such as gastric ulcers from non-steroidal anti-inflammatories or more serious toxicities from overuse of steroids). Other, more potent, anti-proliferative and/or anti-angiogenic drugs such as the anticancer drugs paclitaxel, methotrexate, doxorubicin, camptothecin and etoposide might offer aggressive treatment modalities but use of these drugs against non-life threatening diseases are limited by unwanted toxicities and side effects.

Thus, there has gone unmet a need for compounds, compositions, methods and the like (including delivery approaches) to treat one or more of these diseases, preferably more effectively with few side effects. The present compounds, compositions, methods, etc., provide one or more of these advantages.

SUMMARY

Compositions and methods comprising fucans, and particularly fucoidan, for the treatment of surgical adhesions, arthritis, and psoriasis. The fucans provide significant therapeutic effect for each of these diseases while also providing low side effects.

In one aspect, the present invention provides methods of treating an adhesion in an animal, which can be a human or other desired subject, comprising administering a therapeutically effective amount of a fucan, which can be fucoidan to a disease site potentially having an adhesion. The disease site can be a surgical site, and the fucan can be directly delivered as a composition to the disease site. The fucan can be substantially continuously administered to the disease site via controlled release from a polymeric dosage form, and the polymeric dosage form can be a film, patch, paste, microsphere, implant, gel, spray or liquid. The fucan can be administered as a pharmaceutical composition in a form comprising at least one of a cream, paste, injectable excipient and polymer. (Unless expressly stated otherwise or clear from the context, all embodiments, aspects, features, etc., can be mixed and matched, combined and permuted in any desired manner.)

The fucan can be administered as a pharmaceutical composition comprising the fucan and a therapeutically effective amount of at least one other drug. The drug can be at least one of a paclitaxel, doxorubicin, camptothecin, etoposide, mitoxantrone, methotrexate, menadione, plumbagin, juglone, beta-laperchone cyclosporin, sulfasalazine, steroid, rapamycin, retinoid, docetaxel, and colchicine, antisense oligonucleotide, ribozyme. The therapeutically effective amount of the fucan can be delivered as a part of a composition and the fucan can be from about 0.1% to 35%, 5% to 50%, 20–80%, 80% to 100% w/v of the composition.

The composition further can comprise at least one pharmaceutically acceptable excipient, such as a pluronic, cellulose, alginate, acrylate, hyaluronic acid, polyethylene glycol, injectable excipient, and chitosan. The fucan can be administered orally, directly to the disease site, via injection to the disease site, intraocularly, intraperitoneally, intramuscularly, intraarticularly, intralesionally, subcutaneously, intravaginally, rectally or topically, or otherwise as desired.

In another aspect, the methods comprise treating arthritis, psoriasis or angiogenic eye diseases, comprising administering a therapeutically effective amount of the fucan to a disease site.

In further aspects, the present invention provides pharmaceutical compositions comprising a polymeric dosage form of the fucan comprising a therapeutically effective amount of the fucan and at least one pharmaceutically acceptable excipient selected from the group consisting of a pluronic, alginate, acrylate, hyaluronic acid, polyethylene glycol, injectable excipient, and chitosan. The polymeric dosage form can be a film, paste, microsphere, spray, lotion, liquid, or implant or other form as desired. The pharmaceutical compositions can also comprise a therapeutically effective amount of at least one other drug such as an antisense oligonucleotide, ribozyme and an oligonucleotide RNA inhibitor.

The compositions can be used in the manufacture of a medicament for treating an adhesion, such as a surgical adhesion, arthritis, psoriasis or other diseases as desired. Also provided are methods of manufacturing a medicament able to reduce symptoms associated with at least one of an adhesion, arthritis, and psoriasis in a human patient, comprising combining a pharmaceutically effective amount of a fucan such as fucoidan, a pharmaceutically acceptable excipient or buffer.

These and other aspects, features and embodiments are set forth within this application, including the following Detailed Description and attached drawings. In addition, various references are set forth herein, including in the Cross-Reference To Related Applications, that discuss certain systems, apparatus, methods and other information; all such references are incorporated herein by reference in their entirety and for all their teachings and disclosures, regardless of where the references may appear in this application.

DETAILED DESCRIPTION

Figure 1:
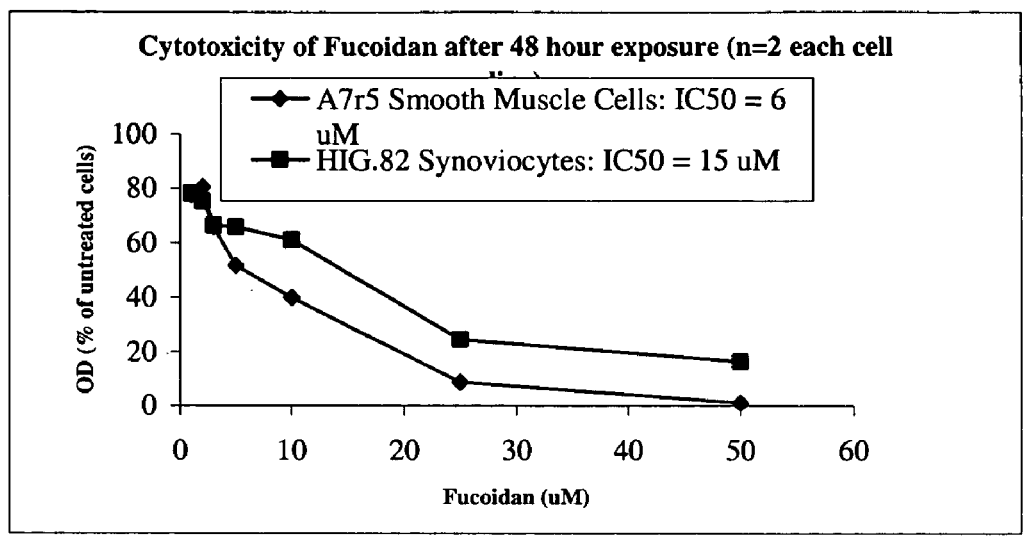
FIG. 1 is a graph of fucoidan inhibition of cell proliferation in synoviocytes and smooth muscle cells after 48 hours exposure.

The present invention includes compositions and methods comprising approaches for inhibiting cell proliferation, inflammatory responses, and angiogenesis using the sulphated polysaccharides known as fucans and can be used to treat surgical adhesions, arthritis, and psoriasis. It appears that fucans such as fucoidan may inhibit neutrophil activation, inhibit inflammatory enzyme release from arthritis associated cells and inhibit angiogenesis in chick membranes and surgical adhesions. Since all cells contain fucose-binding receptors, in some embodiments the fucans are directly delivered to the disease site to provide substantially continuous exposure of target tissue to the fucans (such as fucoidan) via controlled release from polymeric dosage forms. Since fucans can have multiple effects in vivo (in particular affecting blood thrombin and complement) site-directed controlled release of fucans is an alternative to systemic administration that may reduce haematological toxicities.

The following will first generally discuss fucans, adhesions, arthritis and psoriasis, then discuss some embodiments of the invention, then provide some examples.

General Background Discussion About Fucans, Adhesions, Arthritis and Psoriasis

Fucans.

Fucans (including fucoidan) are high molecular weight sulphated polysaccharides extracted from brown seaweeds. These compounds reportedly have multiple inhibitory actions in vivo and in vitro including anti-thrombin, anti-proliferative, anti-complement, anti-cancer and anti-neutrophil migration effects. Fucans may block various binding events at cell surfaces including cell-cell binding through integrin-selectin molecules, or by binding thrombin or complement in the blood or fucose receptors on cell surfaces.

Such activity is thought to be responsible for anti-inflammatory properties via (for example) inhibition of lymphocyte or neutrophil binding to vascular endothelial cells that might prevent the invasion of these cells into a tissue compartment with subsequent inflammation. Patankar, M. S., et al., *J. Biol. Chem.* 268: 21770–21776 (1993); Brandley, B. K., et al., *J. Cell Biol.* 105: 991–997 (1987). Recent studies have also shown that Fucans inhibit vascular smooth muscle cell proliferation, Logeart, D., et al., *Eur. J. Cell Biol.* 74: 376–384 & 385–390 (1997), indicating (but not demonstrating) a possible anti-restenosis potential of these compounds. Fucans have been shown to be slowly internalized in cells following surface binding to both endothelial and smooth muscle cells. Glabe, C. G., et al., *J. Cell Science* 61: 475–490 (1983); Logeart, D., et al., *Eur. J. Cell Biol.* 74: 376–384 (1997).

Riou, D., et al., *Anticancer Res.*, 16 (3A): 1213–1218 (1996); Itoh, H., *Anticancer Res.*, 13 (6A): 2045–2052 (1993); Nishiro, T., et al., *Thromb. Res.*, 62: 765–773 (1991); Blondin, C., et al., *Mol. Immunol.*, 31: 247–253 (1994); Patankar, M. S., et al., *J. Biol. Chem.*, 268: 21770–21776 (1993). In Japan, fucoidan extracted from various seaweeds is marketed as a health food. Fucoidan has been proposed as a cosmetic or dermal agent. JP 01031707 and JP 01085905. Fucoidan has been reported to be a potential anticancer agent. Riou. D., *Anticancer Res.* 16: 3a 1213–18 (1996); Itoh, H., et al., *Anticancer Res.*, 15: 5b 1937–47 (1995). Fucoidan was reported to not inhibit angiogenesis in vitro. Soeda, S., et al., *Biochim. Biophysica Acta* (1): 127–134 (2000).

Similarly, fucoidan was found to stimulate HUVEcell proliferation (in vitro) induced by serum, indicating a possible proangiogenic effect (although inhibition was possible when fibroblast growth factor was present). Giraux, J., et al., *Eur. J. Cell Biol.* 77 4: 352–9 (1998). Studies have also shown that Fucans inhibit endothelial cell monolayer binding. Glabe, C. G., *J. Cell Science,* 61: 475–490 (1983). Since the cells that make up capillaries are endothelial cells, this report indicates that in vitro, some aspects of cell adhesion may be inhibited but these data do not demonstrate any in vivo antiangiogenic effect of fucoidan. Fucoidan has been reported to inhibit the binding of helicobacter to gastric cells hinting at an antigastric ulcer effect. Shibat, H. J., *Nutr. Sci. Vitaminol.* 45: 325–336 (1999).

Other sulphated polysaccharides including branched and linear types are reported to have differential anticoagulant activity. Pereira, M. S., *J. Biol. Chem.* 12: 7656–67 (1999). Dextran sulphate and derivatives have been reported to inhibit cancer cell growth, Bittoun, P., *Carbohydrate Res.* (3–4): 247–255 (1999) and to have anticoagulant effects, Mauray, S., *J. Biomat. Sci. Poly* ed. 9: 373–87 (1998). Sulphated polysaccharides have been proposed as anti-viral agents for use against e.g., AIDS. EP 00293826; JP 01313433.

Adhesions.

Adhesion formation is a complex process in which tissues that are normally separated in the body grow into each other. Surgical adhesions (also known as post-surgical adhesions) develop from the otherwise normal wound healing response of the tissues to the trauma and occur in over two thirds of all abdominal surgical patients. Ellis, H., *Surg. Gynecol. Obstet.* 133:497 (1971); Wiebel, M-A. and Majno, G., *Am. J. Surg.* 126: 345 (1973). The consequences of these adhesions are varied and depend upon the surgical site involved. Problems may include pain, infertility, obstruction of the intestines and even an increased risk of death after cardiac surgery. diZerega, G. S., *Prog. Clin. Biol. Res.* 381: 1–18 (1993); diZerega, G. S., *Fertil. Steril.* 61:219–235 (1994); Dobell, A. R., Jain, A. K., *Ann. Thorac. Surg.* 37: 273–278 (1984).

The process of adhesion formation initially involves the establishment of a fibrin framework and normal tissue repair. The normal repair process allows for fibrinolysis alongside mesothelial repair. However, in surgical adhesion formation the fibrin matrix matures as fibroblasts proliferate into the network and angiogenesis occurs resulting in the establishment of an organized adhesion within 3 to 5 days. Buckman, R. F., et al., *J. Surg. Res.* 21: 67–76 (1976); Raferty, A. T., *J. Anat.* 129: 659–664 (1979).

Inflammatory processes include neutrophil activation in the traumatised tissues, fibrin deposition and bonding of adjacent tissues, macrophage invasion, fibroblast proliferation into the area, collagen deposition, angiogenesis and the establishment of permanent adhesion tissues. Currently, preventive therapies include prevention of fibrin deposition, reduction of inflammation (steroidal and non-steroidal anti-inflammatory drugs) and removal of fibrin deposits.

Interventional attempts to prevent the formation of post-surgical adhesions have included the use of hydroflotation techniques or barrier devices. Hydroflotation involves the instillation of large volumes of polymer solutions such as dextran, Adhesion study group, *Fertil. Steril.* 40:612–619 (1983), or carboxymethyl cellulose, Elkins, T. E., et al., *Fertil. Steril.* 41:926–928 (1984), into the surgical space in an attempt to keep the organs apart. Synthetic barrier membranes made from oxidized regenerated cellulose (Interceed™), polytetrafluroethylene (Gore-tex surgical membrane) and fully resorbable membranes made from a modified hyaluronic acid/carboxymethylcellulose (HA/CMC) combination (Seprafilm™) have also been used to reduce post-surgical adhesion formation in both animals and humans. Burns, J. W., et al., *Eur. J. Surg. Suppl.* 577: 40–48 (1997); Burns, J. W., et al., *Fertil. Steril.* 66:814–821 (1996); Becker, J. M., et al., *J. Am. Coll. Surg.* 183:297–306 (1996). The success of these HA/CMC membranes may derive from their ability to provide tissue separation during the peritoneal wound repair process when adhesions form. The membranes were observed to form a clear viscous coating on the injured tissue for 3–5 days after application, a time period that is compatible with the time course of post-surgical adhesion formation. Ellis, H., *Br. J. Surg.* 50: 10–16 (1963). The intraperitoneal administration of anti-inflammatory agents such as dexamethasone or corticosteroids produced marginal inhibition of adhesion formation diZerega, G. S., *Fertil. Steril.* 61:219–235 (1994); Hockel, M., *Ann. Chir. Gynecol.* 76: 306–313 (1987).

Arthritis.

Arthritis, such as rheumatoid arthritis (RA) is a debilitating chronic inflammatory disease affecting almost 2% of the world's population. This condition is characterized by pain, swelling, synovial cell proliferation (pannus formation), angiogenesis and destruction of joint tissue. In the advanced stage the disease often damages critical organs and may be fatal. The disease involves multiple members of the immune system (macrophages/monocytes, neutrophils, B cells and T cells) complex cytokine interactions and synovial cell malfunction and proliferation. Early aggressive treatment is now recommended with disease modifying anti-rheumatic drugs (DMARDS) such as methotrexate and combinations with cyclosporin or azathioprine. *Arthritis and Rheumatism*, 39(5):713–722 (1996).

Crystal induced arthritis affects almost 1% of the population and is characterised by crystal induced activation of macrophages and neutrophils in the joints and is followed by excruciating pain for many days. The disease progresses so that the intervals between episodes become shorter and morbidity for the patient increase to unacceptable levels. This disease is generally treated symptomatically with NSAIDs. For a more detailed discussion of the pathophysiology of this disease and other forms of inflammatory arthritis see McCarty, et al., Arthritis and Allied Conditions by Lea and Febiger, Philadelphia 1495 (1985).

Psoriasis.

Psoriasis is a common, chronic inflammatory skin disease characterized by raised, thickened and scaly lesions which itch, burn, sting and bleed easily. More than 2% of Americans suffer from psoriasis and patients often have accompanying arthritic conditions. The cause of the disease is unknown and there is no cure for the disease at present. There is evidence supporting the concept of an autoimmune disease. The disease is further characterized by neutrophil activation, cell proliferation and angiogenesis.

Skin cells may follow two routes of growth, normal growth or wound healing. In normal growth, cells are created in the basal layer and move up through the epidermis to the skin surface. Dead cells are shed from the surface at the same rate as new ones form below. During wound healing, accelerated growth and repair is triggered resulting in rapid turnover of skin cells, increased blood supply and inflammation. In some respects psoriasis is an exaggerated wound healing process. If the skin does not shed the skin cells (keratinocytes) as quickly as they are made then a build up may occur. This may lead to scaly lesions and angiogenesis (to increase the blood supply). At the same time, lymphocytes, neutrophils and macrophages may create soreness, swelling and inflammation. Current drug therapies include the use of steroidal and non-steroidal anti-inflammatory agents to treat inflammatory symptoms. Methotrexate and cyclosporin are also used with marginal efficacy. The current cost of treating psoriasis in the USA is more than $3 billion per year.

General Discussion.

The present invention provides fucans (including derivatives and analogues thereof) for the treatment or prevention of surgical adhesions, rheumatoid arthritis, and psoriasis (where treatment as used herein includes both the treatment of existing conditions and the inhibition of potential conditions). As demonstrated in the Examples below, fucans (and in particular, fucoidan) inhibit cell proliferation, inflammatory responses/events and angiogenesis, including for example in surgical adhesions.

In one embodiment, fucans such as fucoidan are used to inhibit or prevent angiogenesis. In another embodiment, fucans such as fucoidan are used to inhibit or prevent inflammatory cell activation, so that the cells that initiate inflammatory responses at such disease sites may be inhibited. This is important, for example, since many diseases such as, for example, osteoarthritis, are not necessarily associated with inflammatory cell accumulation at the disease sites. Thus, such use of fucans can inhibit or prevent the more drawn-out activation of resident macrophages, neutrophils and other inflammation initiating cells that causes the chronic unwanted effects of the disease. Such fucan activities are applied herein to surgical adhesions, arthritis and psoriasis.

In one embodiment of this invention, fucans, including derivatives and analogues thereof, can be formulated in a controlled release formulation to provide for sustained effective concentrations of the agent to be provided at disease sites. In another embodiment, fucoidan is used in the treatment of surgical adhesions. Examples are provided herein. Such examples demonstrate inhibitory action of fucoidan against primary chondrocytes (cells involved in rheumatoid arthritis) derived from fresh cartilage. This indicates the agent has potential as an anti-arthritic agent. In particular, the apparent ability of fucoidan to inhibit collagenase and stromelysin production offers therapeutic approaches where the release of these and/or other metalloproteinases cause medical problems.

In other embodiments, fucoidan can be used in combination with other therapeutic agents to allow for good efficacy against the disease process with low toxicity. For example, in the treatment of surgical adhesions, potent anti-proliferative drugs, such as doxorubicin, camptothecin, etoposide, mitoxantrone, methotrexate, menadione, plumbagin, juglone, beta-laperchone cyclosporin, sulfasalazine, steriods, rapamycin, retinoids, paclitaxel, docetaxel, colchicine and other microtubule inhibitors, and other analogues and derivatives thereof may have unwanted toxicities at concentrations of the drug required for inhibition of adhesion processes without the presence of fucan, but they can be useful in lower concentrations in combination with fucans, such as fucoidan, to achieve desired results.

In another embodiment it is proposed that the fucan can itself be the dosage form of the agent. For example, the fucans can be made in thin films that can be placed directly onto a surgical trauma area so that the slow dissolution of the fucan exposes the tissues to a sustained and effective concentration of the agent. Indeed, such a formulation can act as a controlled release drug delivery system for itself (as the active agent) or for other agents (such as paclitaxel) that can be placed in the formulation. The fucans can also be formed into tablets, capsules, microspheres, pastes, gels, powders, aerosols or given orally, rectally, as a solid or as a solution.

Generally, fucans can be administered alone or as part of a composition by application or injection as a paste, gel, spray, particulate, film, solution, liquid, lotion, cream or implant. Routes and sites of administration include orally, systemically, intraocularly, subcutaneously, intraperitoneally, intramuscularly, intraarticularly, intralesionally, intravaginally, rectally or topically, such as in a patch. These routes may also, in certain cases, be the proposed site of action of the fucan or fucan-drug combination dosage form. The therapeutically effective amount of fucan can be delivered as a part of a composition and can comprises about 5% to 50%, 20–80%, 80% to 100% w/v of the composition. The fucans can be provided in suitable vessels or containers, which in turn can be provided in kits and can also be provided with a label, preferably a label approved by an appropriate government regulatory agency such as the food and drug administration in the United States of America.

For the treatment of adhesions, the fucans or fucan containing compositions can be applied directly to the disease or surgical site as a solution, particulate, suspension, film, paste, gel, spray, liquid, lotion, implant or other desired form. Adhesions can also be treated by the systemic delivery of the fucan using intravenous, subcutaneous, intramuscular, intraperitoneal, oral, or other administration routes as desired. For the treatment of arthritis, the fucans, or fucan containing compositions, can be injected directly into the joint as a paste, gel, spray, liquid, lotion, solution, suspension or other desired form. Arthritis can also be treated or prevented by the systemic delivery of the fucan following intravenous, intramuscular, intraperitoneal, subcutaneous, or oral administration routes.

In some aspects, the present invention provides for treatment of angiogenic diseases of the eye. For example, diabetic retinopathy is a potentially blinding complication of diabetes that damages the blood vessels of the retina followed by new blood vessel growth (angiogenesis) causing blurred vision or retinal destruction. Macular degeneration is caused by the invasion of new blood vessels beneath the retina and is the leading cause of blindness in the USA and Europe with new 200,000 cases per year in the USA and only 15% of those treatable with current laser therapies. The present invention provides, in some embodiments, a pharmacological approach to the treatment of these diseases using the methods and compositions discussed herein as adapted for use with the eye. For example, the fucans can be applied directly to the surface or injected into the eye. Modifications to such systems include chemical crosslinking to slow down the rate of dissolution of the dosage form, or mixture with other excipients such as pluronics, alginates, acrylates, cellulose, hyaluronic acid, polyethylene glycols, chitosan, including analogues and derivatives thereof, and numerous other pharmaceutically acceptable formulating agents.

In still another embodiment, the fucans form a charged aqueous gel with positively charged excipients such as, for example, chitosan or poly-l-lysine. Drugs such as, for example, an antisense oligonucleotide, ribozyme and oligonucleotide RNA inhibitor, can be incorporated into such a gel for application to a disease site. Alternatively such a drug-containing gel, or the drug dissolved in a solution of the fucan, can be dried down and ground up into particles. These particles can then be applied to a disease site to act as a controlled release dosage form, or, the particles can act as a transfection agent since surface bound fucans are taken up into cells. The application of such particles can be further facilitated by the use of pharmaceutically acceptable excipients such as excipients such as pluronics, cellulose, alginates, acrylates, hyaluronic acid, polyethylene glycols, chitosan, injectable excipients, including analogues and derivatives thereof, and numerous polymeric based vehicles.

Regarding transfection and the use of fucans with nucleic acid sequence agents, the advancing area of medicine known as gene therapy is constrained by drug delivery issues whereby gene fragments or nucleic acid chains, such as oligonucleotides including ribozymes, antisense nucleotides and oligonucleotide RNA inhibitors, may have their cell uptake inhibited due to the charge and large molecular weight of these compounds. Recently, the use of microparticles (such as calcium phosphate) containing the gene or nucleic acids have been proposed as transfection agents so that they bind to the cell surface and are taken up by endocytosis or invagination, resulting in cellular entry of the gene or nucleic acid. Most cells contain fucose receptors on the membrane surface. The present invention provides for the use of fucans as transfection agents for nucleic acid chains. In one embodiment, the nucleic acid chain can be bound or encapsulated within a fucoidan microparticle and the particle can be chemically crosslinked to inhibit dissolution before application to the target cell site.

The fucans, either alone or in combination with other drugs, can be used in combination with materials implanted in the body. These materials can include, but are not limited to, numerous medical devices such as catheters, shunts, membranes, stents, sponges, fillings, artificial replacement joints and parts thereof and other orthopedic related implants. Such implants can contain or be coated with fucans, either alone or in combination with other drugs and excipients.

Unless indicated otherwise, except within the claims, the use of "or" includes "and" and vice-versa. Non-limiting terms are not to be construed as limiting unless expressly stated, or the context clearly indicates, otherwise. (For example, "including," "having," and "comprising" typically indicate "including without limitation".) Singular forms, including in the claims, such as "a," "an," and "the" include the plural reference unless expressly stated, or the context clearly indicates, otherwise.

The scope of the present systems and methods, etc., includes both means plus function and step plus function concepts. However, the terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

EXAMPLES

Example 1

The Effect of Fucoidan on Synoviocyte and Smooth Muscle Cell Proliferation In Vitro Proliferation was determined using the dimethylthiazol diphenyltetrazolium bromide salt (MTT) proliferation/cytotoxicity assay.

On day one, 1500–2000 smooth muscle cells (A7r5 rat embryonic thoracic aorta) or synoviocytes (HIG.82 rabbit) were plated per well on a 96-well plate, leaving the first column free of cells (blank). The plate was placed into the 37° C., $CO_2$ incubator. The following day fucoidan was added at various concentrations. No fucoidan was added to the first column (blank) and the second column (untreated column) for control. The cells were exposed for 48 hours. At the end of the exposure period, 50 µl of dimethylthiazol diphenyltetrazolium bromide salt (MTT) dissolved in media was added and allowed to incubate for 4 hours at 37° C. The medium was then aspirated and 200 µl of dimethyl sulfoxide (DMSO) was added. The plate was agitated for 30 minutes and the absorbance read at 562 nm. The optical density measurement was converted to number of cells using a standard plot of optical density with known number of cells and cell viability was expressed as % growth (this value is the % compared to the control cells).

As shown in FIG. 1, the fucoidan induced a concentration dependent inhibition of cell proliferation after 48 hours exposure for both synoviocytes and smooth muscle cells. The inhibitory concentrations that gave 50% effect on proliferation (IC50) were 15 µM and 6 µM respectively.

Example 2

The Effect of Fucoidan on Phorbol Ester Myristate (PMA) Induced Neutrophil Chemiluminescence This experiment incubated freshly prepared human neutrophils with fucoidan at 0.5% w/v followed by stimulation of the cells with the PMA. Stimulation (or activation) of the cells induced superoxide anion generation which could be measured by the emission of light (chemiluminescence). Inhibition of neutrophil function was then determined by the inhibition of chemiluminescence. Hanks buffered salt solution (HBSS) pH 7.4 was used throughout the study. All chemicals were purchased from Sigma Chemical Co. (St. Louis, Mo.) unless otherwise stated. All experiments were performed at 37° C. Neutrophils were prepared from freshly collected, human, citrated whole blood. Briefly, 400 ml of blood were mixed with 80 ml of 4% dextran T500 (Pharmacia LKB, Biotechnology AB Uppsala, Sweden) in HBSS and allowed to settle for 1 h. Plasma was collected continuously and 5 ml applied to 5 ml Ficoll Paque (Pharmacia) in 15 ml polypropylene tubes (Corning, N.Y.). Following centrifugation at 500×g for 30 min, the neutrophil pellets were washed free of erythrocytes by 20 s of hypotonic shock. Neutrophils were resuspended in HBSS, kept on ice and used for experiments within 3 h. Neutrophil viability and purity was always greater than 90%.

Cells were incubated with various concentrations of fucoidan for 15 minutes at 37° C. before addition of PMA. Chemiluminescence studies were performed at a cell concentration of $5 \times 10^6$ cells per ml in HBSS with PMA at 0.5 µM. To the tubes were added 10 µL of luminol dissolved in 25% DMSO in HBSS to give a final concentration of 1 mM and the samples were mixed to initiate neutrophil activation. Chemiluminescence was monitored using an LKB Luminometer (Model 1250) at 37° C. with shaking immediately prior to measurements. Control tubes contained cells, fucoidan and luminol.

Figure 2:
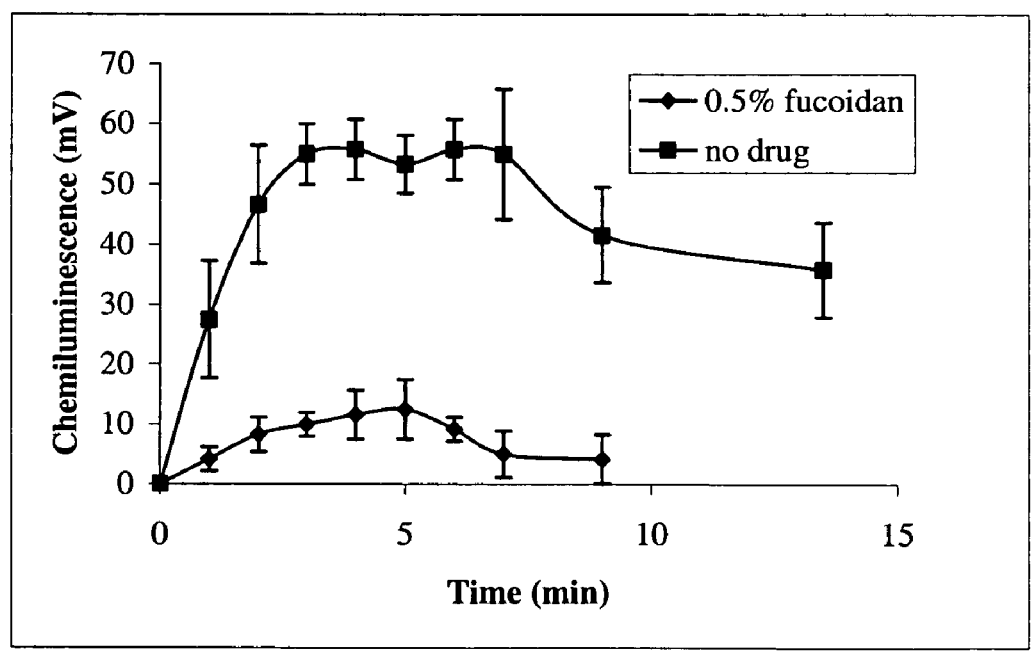
FIG. 2 is a graph of fucoidan inhibition of phorbol ester myristate (PMA) induced neutrophil activation.

Fucoidan strongly inhibited PMA induced neutrophil activation as shown in FIG. 2. The data is for three separate PMA-neutrophil incubations. These data demonstrate an anti-inflammatory effect of fucoidan.

Example 3

The Effect of Fucoidan on IL-1 Induced Collagenase Gene and Stromelysin Gene Expression in Chondrocytes This assay measures the levels of RNA for two metalloproteinases, collagenase and stromelysin. Over-expression of these genes results in secretion of these two enzymes from articular chondrocytes and may represent part of the pathophysiology of rheumatoid arthritis. Agents that inhibit overexpression of collagenase and stromelysin are potential antiarthritic agents. This antiarthritic potential may be lessened if the agent also inhibits proteoglycan gene expression significantly. Proteoglycan gene expression is part of the normal physiology of chondrocytes. Primary chondrocyte culture was freshly isolated from calf cartilage. The cells were plated (at $2.5 \times 10^6$/ml) in 100×20 mm culture dishes and incubated in Ham's F12 medium containing 5% fetal bovine serum (FBS) overnight at 37° C. The cells were starved with serum-free medium overnight. The cells were pretreated with camptothecin at concentrations of $10^{-6}$ M, $10^{-7}$ M and $10^{-8}$ M for 6 hours. Then IL-1 (20 ng/ml) was added to each plate and the plates were incubated for an additional 18 hours. Total RNA was isolated by the acidified guanidine isothiocyanate method and subjected to electrophoresis on a denatured gel. Denatured RNA samples (15 µg) were analyzed by gel electrophoresis in a 1% denaturing gel, transferred to a nylon membrane, and hybridized respectively with the $^{32}$P-labelled collagenase cDNA probe, $^{32}$P-labelled stromelysin cDNA probe, $^{32}$P-labelled proteoglycan cDNA probe and $^{32}$P-labelled glyceraldehyde phosphate dehydrogenase (PAGDH) cDNA. The PAGDH levels acted as an internal standard to ensure roughly equal loading. The experimental results on X-ray films were scanned and analyzed with HP ScanJet.

Figure 3:
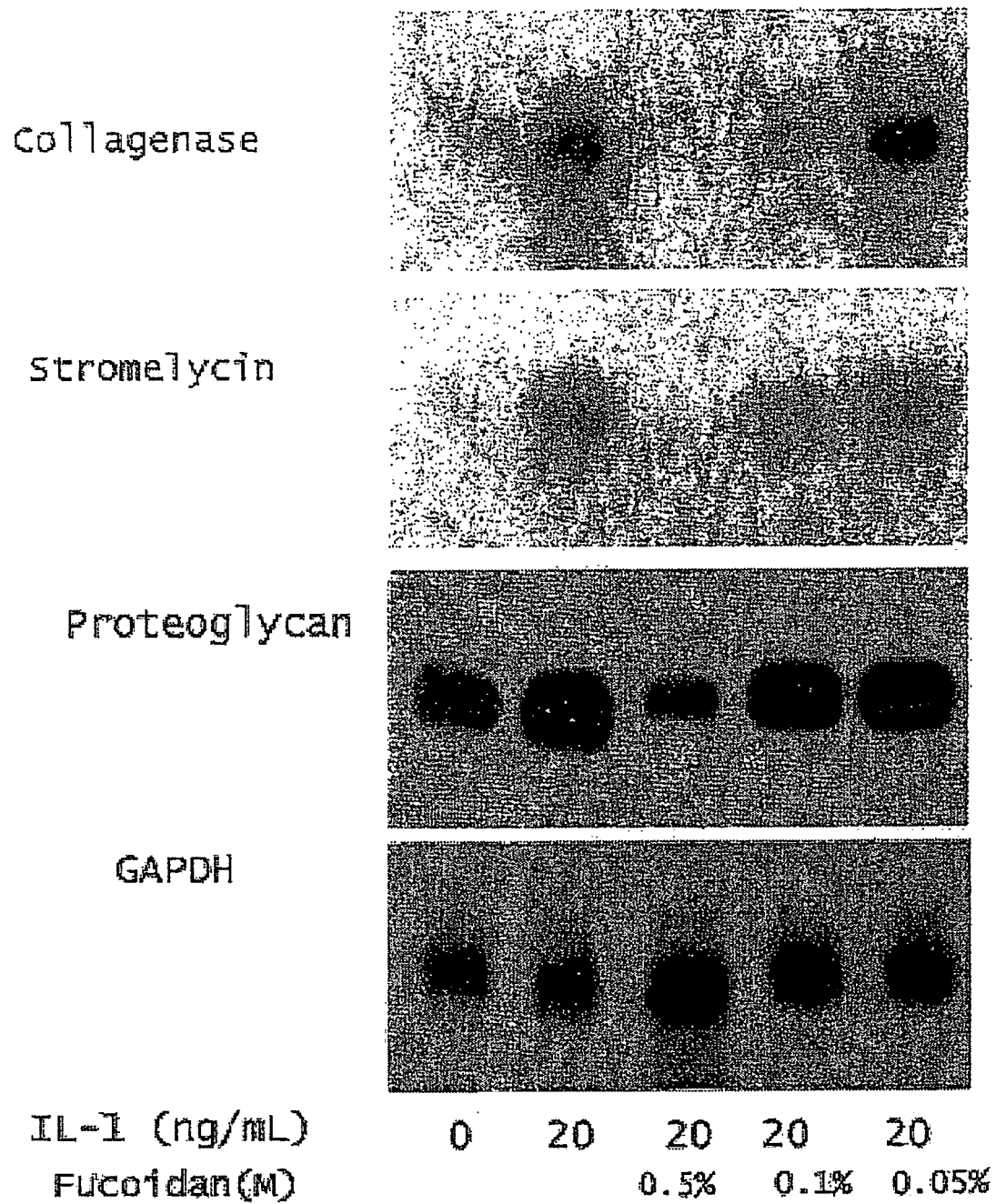
FIG. 3 is a photograph depicting fucoidan inhibition of collagenase and stromelysin expression at a concentration of 0.5% w/v without excessive inhibition of proteoglycan expression.

Fucoidan fully inhibited collagenase and stromelysin expression at a concentration of 0.5% w/v without excessive inhibition of proteoglycan expression as shown in FIG. 3. At a concentration of 0.1% w/v there was potent inhibition of collagenase and stromelysin expression without any inhibitory effect on proteoglycan expression. These data demonstrate an anti-inflammatory effect of fucoidan.

Example 4

The Effect of Fucoidan on Angiogenesis in the Chorioallantoic Membrane of the Chick Embryo (CAM Assay)

Fertilized chicken eggs were obtained from a local hatchery and placed in an incubator with an automatic rotator at 37° C. for 3.5 days prior to deshelling or windowing.

Sheets of sterile waxed paper were placed onto the window that was created in the air space and were used to prevent contamination and dehydration of the egg contents. These sheets, measuring 4 cm×4 cm, were sterilized by spraying them with 70% ethanol and allowing them to dry in the laminar flow hood. After three days the eggs were manually rotated in the incubator such that their sharp end was facing up for 5–10 minutes to allow detachment of the egg contents from the inner membrane. Using 70% ethanol and Kimwipes, the entire eggshell was wiped down to help clean and sanitize the outside of the egg. Inside a laminar flow hood, the egg was held with the blunt side up and a hole was made in the blunt end of the egg by carefully cracking the shell with the end of forceps. The shell remnants were gently removed with forceps to form a hole in the blunt end. This circular hole was made as large as 2 to 3 cm in diameter without damaging the inner membrane. Once the hole was created in the shell, the inner shell membrane (which houses the egg contents) was gently torn and removed using the forceps, taking care not to damage the chorioallantoic membrane (CAM) (which houses the yolk and developing chick embryo).

The hole was then covered with the sheet of sterilized parafilm wax paper by gently stretching the parafilm and then placing it around the hole. The egg was then placed in the egg rack in the incubator (37° C.) and positioned in such a way as to prevent rotation. After 6 days each egg was removed one by one from the incubator (blunt side up), and the parafilm covering the window was removed for direct access to the CAM, which originates from the hind gut of the embryo. Fucoidan-loaded poly(epsilon-caprolactone) (PCL) pellets were manufactured by melting PCL at 60° C. and physically blending the fucoidan into the PCL and allowing the pellets to harden by cooling to room temperature. The fucoidan pellets were placed onto the growing capillary bed of the CAM. The egg contents were then resealed with the parafilm sheet and placed back into the 37° C. incubator. After 2 more days, analysis of the CAM vasculature was recorded (48 hours after placing the drug onto the CAM capillary bed). The effect of the drug on the CAM was rated using an avascular scale, which grades the effect of the drug as 0, 1, 2, or 3. The values of the avascular scale describe the following:

0 No antiangiogenic activity

1 Microvessel reduction

2 Small avascular zone measuring the size of the drug pellet (2 mm in diameter)

3 Avascular zone measuring 4–5 mm in diameter.

Fucoidan potently inhibited angiogenesis in the CAM as shown in Table 1. Concentrations of fucoidan as low as 2% w/w in PCL either partially or fully inhibited angiogenesis in 4 or 2 CAM's respectively.

TABLE 1

Antiangiogenic Activity of Fucoidan. The number in each column shows the number of eggs (CAM's) showing none, partial or maximal inhibition of angiogenesis.

| Drug Concentration | Antiangiogenic Activity | | |
|---|---|---|---|
| | None (0) | Partial (1–2) | Maximal (3) |
| Fucoidan 2.0% | — | 4 | 2 |
| Fucoidan 5.0% | — | 1 | 4 |
| Fucoidan 15.0% | — | 2 | 3 |
| Fucoidan 30.0% | — | 2 | 1 |
| Control | 11 | — | — |

These data demonstrate an antiangiogenic activity of fucoidan and show that a polymeric slow release formulation of fucoidan is an effective method of releasing therapeutically effective concentrations of the drug without inducing undue toxicity.

Example 5

The Encapsulation of Fucoidan in Ethylene Vinyl Acetate Films and Polycaprolactone Paste Five mg of fucoidan (Sigma) and 45 mg of ethylene vinyl acetate (EVA, molecular weight approximately 50 k, Polysciences) were dissolved/suspended in 1 ml of dicloromethane. Two hundred μl of the solution was pipetted onto 1 cm diameter teflon discs and allowed to dry overnight (solvent evaporation) to form thin elastic films to give approximately 10 mg films with an approximate thickness of 100 μm.

Figure 4:
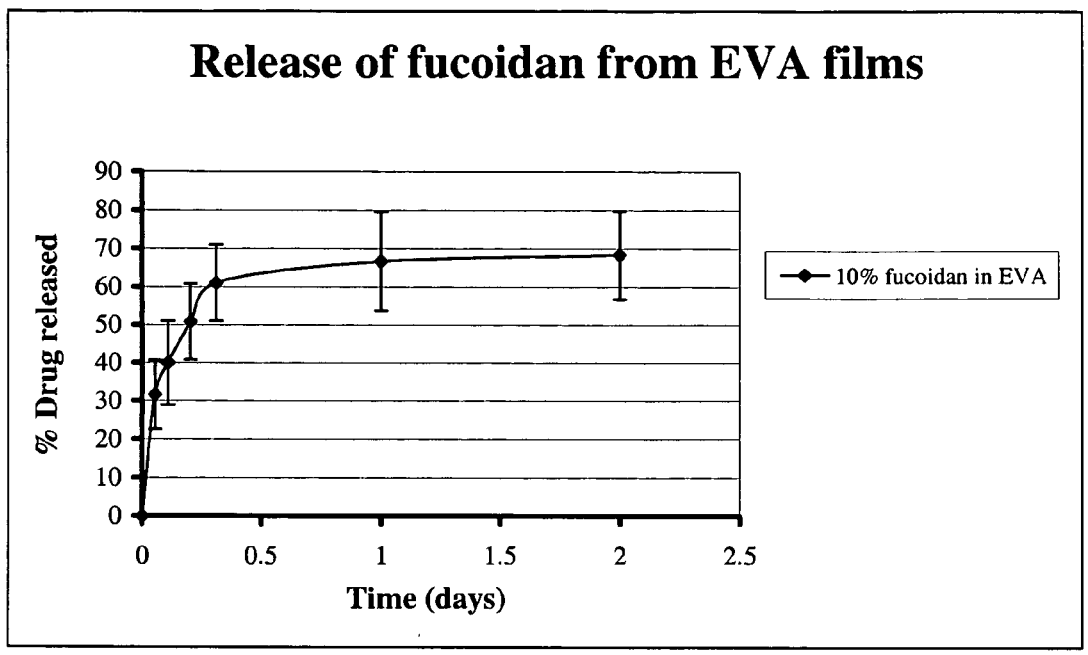
FIG. 4 is a graph of fucoidan release from ethylene vinyl acetate film.

The rate of drug release from these films was measured by placing 5 mg sections of films in 20 ml capped glass tubes containing 10 ml of phosphate buffered saline (PBS) pH 7.4. The tubes were capped, and placed in an orbital shaker at 37° C. At specified times, the tubes were removed and the amount of drug released was analysed by absorbance spectroscopy. The release profile of fucoidan (FIG. 4) was characterized by an initial burst of drug release followed by a slow sustained release. This dosage form of fucoidan represents a biocompatible, biodegradable, injectable formulation of the drug that releases the drug in a controlled manner.

PCL paste: Fucoidan was blended into polycaprolactone (PCL, Birmingham polymers, molecular weight 54K) at 60° C. by spatula levigation at a concentration of 10% w/w. This mixture was then pipetted into 1 ml plastic syringes and allowed to cool. This formulation could be injected through an 18 gauge needle at 56° C.

Figure 5:
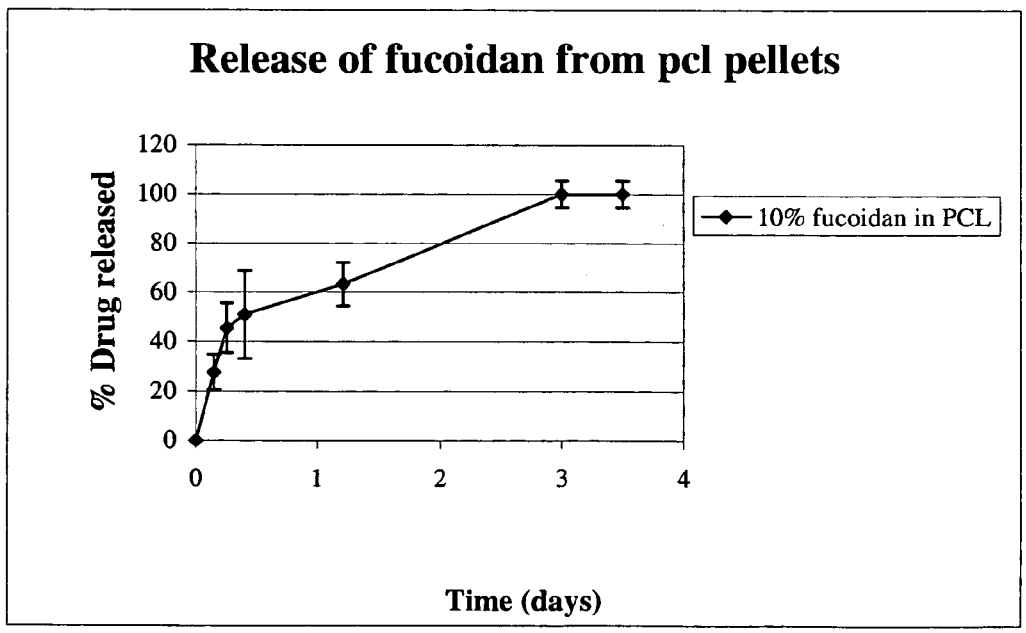
FIG. 5 is a graph of fucoidan release from polycaprolactone paste.

To measure drug release from the PCL paste, 10 mg aliquots of molten paste were injected onto the base of 15 ml glass tubes and allowed to cool and set. Fifteen ml of PBS was added to each tube and the tubes were capped, and tumbled end over end in a 37° C. oven. At specified times, the tubes were removed and the amount of drug released was analysed by absorbance spectroscopy. The release profiles of fucoidan is shown in FIG. 5. The release of fucoidan was characterized by an initial burst of drug release followed by a slow sustained release. This dosage form of fucoidan represents a biocompatible, biodegradable, injectable formulation of the drug that releases the drug in a controlled manner.

Example 6

Fucoidan Loaded Membranes for the Treatment of Surgical Adhesions in Rats

The rat cecal side wall model of surgical adhesions was used to investigate the effect of fucoidan on surgical adhesions. In this model, 16 rats were split into two groups of 8. After surgical trauma, the rats were immediately treated with crosslinked hyaluronic acid (HA) films containing fucoidan or were untreated (control group).

Materials and Methods. Medical grade sodium hyaluronate was obtained from Lifecore Scientific. All solvents were HPLC grade and obtained from Fisher. Plastic Petri dishes were obtained from Fisher Scientific. Ethyl-3-(dimethylamino) carbodiimide (EDAC) and fucoidan were obtained from Sigma (St. Louis. Mo.).

Preparation of Films. Fucoidan loaded films were made by preparing a solution of 0.6% w/v fucoidan, 0.4% w/v sodium hyaluronate and 0.15% w/v glycerol in water. Control films (no fucoidan) were made by preparing a solution or mixture of 0.4% w/v sodium hyaluronate and 0.15% w/v glycerol in water. Fucoidan loaded films and control films were cast from these solutions by pipetting 4 g of each solution into separate 2.5 cm diameter plastic Petri dishes and drying for 24 hours at 60° C. The crosslinking agent EDAC was included at 4 mM (final concentration). Each dried film was then carefully removed from the Petri dish using a surgical blade.

Sterilization. Films were packed between 5 cm×5 cm weighing paper (Fisher scientific) and heat sealed in plastic bags. Films were then terminally sterilized using gamma irradiation from a cobalt-60 source and exposed to 2.5 Mrad of radiation with cooling of the sealed tube on ice.

Animal Studies. Surgical trauma was induced as follows: 16 mature Sprague Dawley rats, each weighing 225–350 g were obtained from Charles River Laboratories, Wilmington, Mass. Only animals which appeared grossly normal (i.e., showing a clean unruffled coat, bright clear eyes and an active posture) were used in the study. Animals were randomly assigned to one of two groups, weighed and anesthetized with a single injection of ketamine hydrochloride (6 mg/kg), administered in the large muscle of the thigh. The abdomen was shaved and cleaned with alcohol. A 4 cm incision was made in the skin beginning approximately 2 cm caudal to the linea alba while the muscle was tended with forceps. The cecum was abraded four times on the ventral and dorsal surfaces with a mechanical abrading device, which permits operator independent, controlled abrasion over a defined area. Adhesions to the cecum were evaluated and scored according to a predefined scoring system:

0=no adhesions
1=filmy adhesion with easily identifiable plane
2=mild adhesion with freely dissectable plane
3=moderate adhesion with difficult dissection of plane
4=dense adhesion with non-dissectable plane
(Grade 1 adhesions are the lowest level of discernable adhesion (a filmy adhesion with an identifiable plane)).

Following abrasion of the cecum, animals in Group 1 received no treatment. Animals in Groups 2 received fucoidan-HA films discussed above. The films were wrapped around the cecum. The incisions were then closed with 3.0 Dexon suture. Seven days postoperatively, the animals were euthanised and evaluated for the presence of grade 2 (or higher) postoperative adhesions. Grade 2 adhesions were defined as mild adhesions with a freely dissectable plane.

Results:

TABLE 2

| Group | % With Adhesions ≧ 2 | Mean Incidence ± SEM | % With No Adhesions |
|---|---|---|---|
| Control | 75 | 1.4 ± 0.4 | 25 |
| Fucoidan loaded Membrane | 38 | 0.5 ± 0.2 | 50 |

Membranes only covered about half of the cecum
No abnormalities were noted upon necropsy (no residual material, no ascites, no signs of abnormal healing, either on the cecum or at the midline incision)

The results demonstrate the effective inhibition of adhesion formation by fucoidan loaded films because the mean incidence of adhesions was reduced and the % of rats with no adhesions was increased in fucoidan treated rats. Fucoidan loaded films that fully cover the cecum might be even more effective at inhibiting adhesion formation.

From the foregoing, it will be appreciated that, although specific embodiments have been discussed herein for purposes of illustration, various modifications may be made without deviating from the spirit and scope of the disclosure. Accordingly, the systems and methods, etc., include such modifications as well as all permutations and combinations of the subject matter set forth herein and is not limited except as by the appended claims.

We claim:

1. A method of treating a fibrous adhesion in an animal comprising selecting a fucan to inhibit the fibrous adhesion and administering a therapeutically effective amount of the fucan to the site of a wound of the animal.

2. The method of claim 1 wherein the fucan is fucoidan.

3. The method of claim 1 or 2 wherein the site is a surgical site, and the fucan is directly delivered as a composition to the site.

4. The method of claim 1 or 2 wherein the fucan is substantially continuously administered to the site via controlled release from a polymeric dosage form.

5. The method of claim 4 wherein the polymeric dosage form comprises a film, patch, paste, microsphere, implant, gel, spray or liquid.

6. The method of claim 1 wherein the fucan is administered as a pharmaceutical composition in a form comprising at least one of a cream, paste, and injectable excipient.

7. The method of claim 1 or 2 wherein the fucan is administered as a liquid pharmaceutical composition.

8. The method of claim 1 or 2 wherein the therapeutically effective amount of the fucan is delivered as a part of a composition and the fucan comprises about 20–80% w/v of the composition.

9. The method of claim 1 or 2 wherein the therapeutically effective amount of the fucan is delivered as a part of a composition and the fucan comprises about 80% to 100% w/v of the composition.

10. The method of claim 1 or 2 wherein the therapeutically effective amount of the fucan is delivered as a part of a composition and the fucan comprises about 5% to 50% w/v of the composition.

11. The method of claim 1 or 2 wherein the composition further comprises at least one pharmaceutically acceptable excipient selected from the group consisting of a pluronic, cellulose, alginate, acrylate, hyaluronic acid, polyethylene glycol, and chitosan.

12. The method of claim 1 or 2 wherein the fucan is administered directly to the site.

13. The method of claim 1 or 2 wherein the fucan is administered via injection to the site.

14. The method of claim 1 or 2 wherein the fucan is administered orally, intraocularly, subcutaneously, intraperitoneally, intramuscularly, intravenously, intraarticularly, intralesionally, intravaginally, rectally or topically.

15. The method of claim 1 or 2 wherein the animal is a human.

* * * * *